(12) United States Patent
Kolstad et al.

(10) Patent No.: US 12,371,411 B2
(45) Date of Patent: *Jul. 29, 2025

(54) WATER AND THERMAL TREATMENT OF PURIFIED 2,5-FURANDICARBOXYLIC ACID

(71) Applicant: Furanix Technologies B.V., Amsterdam (NL)

(72) Inventors: Jeffrey John Kolstad, Amsterdam (NL); Ana Sofia Vagueiro De Sousa Dias, Amsterdam (NL); Johannes Maria Franciscus Sijben, Amsterdam (NL); Ana Rita Martins Guerreiro Rocha Almeida, Amsterdam (NL); Ines Dacil Gonzalez Jimenez, Amsterdam (NL)

(73) Assignee: Furanix Technologies B, V., Amsterdam (NL)

(*) Notice: Subject to any disclaimer, the term of this patent is extended or adjusted under 35 U.S.C. 154(b) by 605 days.

This patent is subject to a terminal disclaimer.

(21) Appl. No.: 17/780,080

(22) PCT Filed: Dec. 18, 2020

(86) PCT No.: PCT/EP2020/087075
§ 371 (c)(1),
(2) Date: May 26, 2022

(87) PCT Pub. No.: WO2021/213206
PCT Pub. Date: Jun. 24, 2021

(65) Prior Publication Data
US 2023/0002338 A1 Jan. 5, 2023

(30) Foreign Application Priority Data
Dec. 20, 2019 (EP) .................... 19218639

(51) Int. Cl.
*C07D 307/68* (2006.01)
*C08G 63/672* (2006.01)

(52) U.S. Cl.
CPC ......... *C07D 307/68* (2013.01); *C08G 63/672* (2013.01); *C07B 2200/13* (2013.01)

(58) Field of Classification Search
CPC .. C07D 307/68; C08G 63/672; C07B 2200/13
(Continued)

(56) References Cited

U.S. PATENT DOCUMENTS

2018/0155308 A1* 6/2018 Almeida ................ C07B 41/02

FOREIGN PATENT DOCUMENTS

| CN | 105936630 A | 9/2016 |
| CN | 108779088 A | 11/2018 |

(Continued)

OTHER PUBLICATIONS

Chinese Patent Application No. 202080090888.6, First Office Action, dated May 27, 2024, 25 pages.
(Continued)

*Primary Examiner* — Taylor V Oh
(74) *Attorney, Agent, or Firm* — Hoffmann & Baron, LLP (57) ABSTRACT

Thermal treatment of purified 2,5-furandicarboxylic acid (FDCA) for producing a carboxylic acid composition, the process comprising the steps of providing or producing a thermal treatment composition comprising a purified carboxylic acid composition and a water containing treatment solvent composition; subjecting the thermal treatment composition to an elevated temperature, wherein the FDCA is partially dissolved, and cooling the treated composition and separating at least a portion of the FDCA from the treated composition to obtain a carboxylic acid composition.

10 Claims, 2 Drawing Sheets

(58) Field of Classification Search
USPC .......................................................... 549/485
See application file for complete search history.

(56) References Cited

FOREIGN PATENT DOCUMENTS

| | | | |
|---|---|---|---|
| CN | 109797434 A | | 5/2019 |
| EP | 3 505 514 A1 | | 7/2019 |
| JP | 2017-190316 A | | 10/2017 |
| KR | 20120107573 | * | 10/2012 |
| WO | 2011/043660 A2 | | 4/2011 |
| WO | 2014/014981 A1 | | 1/2014 |
| WO | 2015/030590 A1 | | 3/2015 |
| WO | 2016/195499 A1 | | 12/2016 |
| WO | 2016/195500 A1 | | 12/2016 |
| WO | 2017/003293 A1 | | 1/2017 |

OTHER PUBLICATIONS

Intellectual Property India, Office Action, Patent Application No. 202217038147, dated Mar. 11, 2025, 8 pages.

* cited by examiner

WATER AND THERMAL TREATMENT OF PURIFIED 2,5-FURANDICARBOXYLIC ACID

CROSS-REFERENCE TO RELATED APPLICATIONS

This application is the National Stage of International Application No. PCT/EP2020/087075, filed Dec. 18, 2020, which claims the benefit of European Application No. 19218639.3, filed Dec. 20, 2019, the contents of which is incorporated by reference herein.

TECHNICAL FIELD

The present invention relates to a process for producing a carboxylic acid composition, the respective carboxylic acid composition and a starting material for the production of polyalkylenefuranoate.

BACKGROUND 2,5-Furandicarboxylic acid (FDCA) is known in the art to be a highly promising building block for replacing petroleum-based monomers in the production of high performance polymers. In recent years FDCA and the novel plant-based polyester polyethylenefuranoate (PEF), a completely recyclable plastic with superior performance properties compared to today's widely used petroleum-based plastics, have attracted a lot of attention. These materials could provide a significant contribution to reducing the dependence on petroleum-based polymers and plastics, while at the same time allowing for a more sustainable management of global resources. Correspondingly, comprehensive research was conducted in the field to arrive at a technology for producing FDCA and PEF in a commercially viable way, in order to allow successful marketing of these promising materials.

FDCA is typically obtained as crude carboxylic acid composition by oxidation of molecules having furan moieties, e.g. 5-hydroxymethylfurfural (5-HMF) and the corresponding 5-HMF esters or 5-HMF ethers and similar starting materials, that are typically obtained from plant-based sugars, e.g. by sugar dehydration. A broad variety of oxidation processes is known from the prior art, that comprises e.g. enzymatic or metal catalysed processes.

One of the most established techniques in the field uses a catalyst system comprising cobalt, manganese and bromine to oxidize compounds having a furan moiety to FDCA using oxygen or air as an oxidizing agent. Respective processes that are applicable to a wide variety of starting materials are for example disclosed in WO 2014/014981 A1 or WO 2011/043660 A1.

In most cases, the purity obtainable for the crude carboxylic acid composition in the above-mentioned processes is not sufficient for achieving the required degree of purity that is needed for the polymerisation of FDCA to PEF or other high performance polymers. Therefore, purification processes have been developed for further purifying the crude carboxylic acid compositions in order to produce a purified carboxylic acid composition. These processes comprise e.g. hydrogenation steps, post oxidation steps, distillation steps, recrystallization steps or similar methods, oftentimes combined with comprehensive purification schemes with several steps of washing and isolating the obtained carboxylic acid composition. Exemplary purification processes are e.g. disclosed in WO 2014/014981 A1 or WO 2016/195499 A1.

Despite the comprehensive effort of improving existing processes for obtaining a sufficiently pure FDCA (sometimes labelled polymer grade FDCA) the results obtained by the known purification processes are oftentimes not completely satisfactory. While prior art processes for purifying crude FDCA oftentimes provide good results with respect to 5-formyl-2-furancarboxylic acid (FFCA), i.e. in most cases the dominant impurity obtained by incomplete oxidation of the starting materials, these methods in many cases do not achieve sufficient reduction of other common impurities, some of which can be present in significant amounts based on the process used for oxidation. In particular, several prior art processes do not provide for a sufficient reduction of the amount of 2-furancarboxylic acid (FCA), i.e. the monoacid that corresponds to FDCA, that is oftentimes produced during oxidation, e.g. by decarboxylation of FDCA.

Furthermore, it was accepted in the field that solid FDCA particles that are obtained with prior art purification processes often have less desirable physical and mechanical properties. These properties comprise e.g. larger amounts of undesirable fines in the solid product, i.e. very small particles that are oftentimes shaped like shards of broken glass, and generally a lower strength of the obtained particles. Other less desirable properties comprise e.g. agglomerates which can be formed during isolation and drying procedures, resulting in unusually large particles. These properties make the handling of particles significantly more difficult and costly than for the most common petroleum-based diacids. For example, it is more difficult to pour the solid FDCA product or to feed it through tubes and pipes. Furthermore, the storage properties of the solid FDCA are also less desirable as the particles oftentimes tend to stick to each other.

Probably one of the most significant drawbacks of less desirable mechanical and physical properties is that it can be less easy to mix the solid FDCA with the other starting materials as well as the catalyst that are required for producing the polymer, leading to less a homogeneous starting mixture having concentration gradients which can negatively impact both the required reaction time and the quality of the resulting polymer.

The less desirable mechanical and physical properties are attributed by the inventors of the present invention to the shape and the low strength of the particles as well as to the particle size distribution in the obtained purified FDCA compositions. These exhibit in most cases plate-like particles with a high amount of fines. Until now, no expedient approach is known in the art for efficiently improving the mechanical and physical properties of the purified FDCA.

The above-mentioned problems with respect to the less desirable purity and mechanical properties of the solid FDCA tend to occur independent of the starting material that is used for the production of FDCA.

However, in recent years it was discovered that a promising approach for arriving at FDCA employs a significant amount of 5-HMF ether as starting material for the oxidation. As a result, the crude carboxylic acid composition obtained in such processes does not only comprise the free diacid, i.e. FDCA, but also includes a significant amount of the mono alkyl ester of FDCA, wherein currently those processes appear to be most established that result in significant amounts of the mono methyl ester of FDCA (FDCA-Me). While the respective process has several benefits over comparable processes that do not yield mono alkyl esters of FDCA, the above-described drawbacks with respect to the purity and the mechanical properties of the solid FDCA obtained in these processes are particularly undesirable. We now have found that the mono alkyl ester of FDCA seems to be among those impurities that are insufficiently removed by many prior art purification processes. As a consequence, purified FDCA compositions that are produced using the above-mentioned technology, tend to comprise significant amounts of FCA and FDCA-Me, wherein in a subsequent polymerisation reaction FCA is a potential chain terminator and FDCA-Me can produce methanol that could cause dangerous side reactions. Furthermore, we found that the presence of FDCA-Me, even in minor amounts, can lead to mechanical and physical properties of the solid FDCA, that are more unfavourable than those that are found for purified FDCA compositions that do not comprise FDCA-Me. In summary, the above-mentioned deficiencies of the prior art processes are especially pronounced for processes that comprise FDCA-Me in the crude and/or purified carboxylic acid composition.

In view of the above described problems, there was a long-felt need to overcome the respective disadvantages of the prior art processes. An objective of the present invention was to provide for an improved process that further increases the purity of the obtained carboxylic acid composition, in particular with respect to FCA and/or FDCA-Me impurities. Another objective was to provide for a process that yields a carboxylic acid composition with good mechanical and physical properties and therefore allows for an efficient handling of the solid product and a favourable behaviour of the solid FDCA in the subsequent polymerisation reaction. It was a further objective of the present invention to provide for a process that can readily be combined with existing oxidation and purification processes and can be conducted in a continuous, semi-continuous or batch fashion.

It would be desirable if the additional process steps could be conducted in a resource efficient way and would produce only minor amounts of waste themselves. Likewise, it would be desirable to provide a process that uses mostly those chemical compounds and starting materials that are employed during other steps of the remaining production process as well, e.g. during oxidation or purification, in order to reduce storage costs and to minimize the amount of different substances that need to be handled at the production plant.

Likewise, it would be preferred if the respective process would require a limited amount of energy, would employ mostly non-corrosive substances and could be operated in a particular safe way, minimizing health risks and exposure of dangerous substances to the environment. Aside from the desire for a particular efficient purification with respect to FCA and/or FDCA-Me, it would also be desirable that the process is able to remove a broad variety of possible impurities in order to efficiently supplement the prior art purification methods.

Furthermore, it was an objective of the present invention to provide a carboxylic acid composition that not only has a high purity but also exhibits favourable physical and/or mechanical properties that allow for an efficient use as starting material in subsequent polymerization reactions.

Correspondingly, it was another objective of the present invention to provide a starting material for the production of polyalkylenefuranoate that allows for reduced reaction times during the polymerisation and/or yields a particular favourable product.

DISCLOSURE OF THE INVENTION

We now have found a process for producing a carboxylic acid composition comprising 2,5-furandicarboxylic acid, the process comprising the steps:

a) providing or producing a crude carboxylic acid composition comprising 2,5-furandicarboxylic acid and 5-formyl-2-furancarboxylic acid;
b) purifying the crude carboxylic acid composition to produce a purified carboxylic acid composition comprising 2,5-furandicarboxylic acid, that is preferably at least partially solid, more preferably at least 5% solid, most preferably at least 80% solid, wherein the purifying comprises at least one step selected from the group consisting of:
   hydrogenating at least a portion of the 5-formyl-2-furancarboxylic acid;
   oxidizing at least a portion of the 5-formyl-2-furancarboxylic acid;
   recrystallization of at least a portion of the 2,5-furandicarboxylic acid; and
   hydrolyzing of dialkyl ester of 2,5-furandicarboxylic acid;
c) providing or producing a treatment solvent composition comprising more than 95% by weight of water, preferably more than 98%, more preferably more than 99%, with respect to the weight of the treatment solvent composition;
d) providing or producing a thermal treatment composition comprising the purified carboxylic acid composition and the treatment solvent composition;
e) subjecting the thermal treatment composition to an elevated temperature in the range of 140 to 200° C. for a time in the range of 5 to 240 min, wherein the percentage of dissolved 2,5-furandicarboxylic acid, relative to the total amount of 2,5-furandicarboxylic acid, is in the range of 10 to 80% to obtain a treated composition; and
f) cooling the treated composition to a temperature in the range of 20 to 80° C. and separating at least a portion of the 2,5-furandicarboxylic acid from the treated composition to obtain a carboxylic acid composition and a treatment mother liquor comprising water. Carboxylic acid composition which can be or is obtained by the process will be a carboxylic acid composition modified compared to the crude carboxylic acid composition of step a) and the purified carboxylic acid composition of step b). Modified carboxylic acid composition is hereinafter referred to as carboxylic acid composition.

The above process provides an additional process step in the production of carboxylic acid compositions comprising FDCA that is conducted after both the oxidation and the purification step. The additional process step that is part of the present process is a specific thermal treatment and comprises mixing purified carboxylic acid composition with a treatment solvent composition and subjecting to a thermal treatment.

The thermal treatment of the present process is conducted in a way that a percentage of FDCA is dissolved during the thermal treatment in the treatment solvent composition while the residual FDCA remains as a solid precipitate. Without wishing to be bound by theory, it is believed that it is the chemical equilibrium and exchange between dissolved and precipitated FDCA in combination with the prolonged thermal treatment, that results in a particular favourable particle shape, increased particle strength and/or a beneficial particle size distribution of the solid FDCA that is obtained after thermal treatment. Surprisingly, the purity of the materials which were obtained in a process with a specific percentage of FDCA dissolved during thermal treatment was found to be superior to the purity of materials which were treated with a process of full dissolution of the FDCA.

MODES FOR CARRYING OUT THE INVENTION

Hereinafter, the subject-matter of the invention is discussed in more detail, wherein preferred embodiments of the invention are disclosed. Thereby, it is particularly preferred to combine two or more preferred embodiments to obtain an especially preferred embodiment. Correspondingly, especially preferred is a process according to the invention that defines two or more features of preferred embodiments of the present invention.

A carboxylic acid composition is a carboxylic acid composition that, when compared to the purified carboxylic acid composition, comprises a reduced amount of at least one furanic impurity, i.e. any substance with a furan moiety that is not 2,5-furandicarboxylic acid, and/or exhibits improved mechanical and/or physical properties.

Step a) of the processes according to the invention is the provision or production of a crude carboxylic acid composition comprising FDCA and FFCA, i.e. the most relevant impurity that is produced during oxidation of the starting materials due to an incomplete oxidation. According to the invention the crude carboxylic acid composition can be provided, e.g. taken from another process or from a separate facility, or produced using one of the several processes for obtaining a crude carboxylic acid composition comprising FDCA and FFCA known from the prior art. The process of the present invention is not limited with respect to the oxidation method that is used for obtaining the crude carboxylic acid composition. However, the crude carboxylic acid composition is preferably produced by oxidation of a compound having a furan moiety, preferably 5-hydroxymethylfurfural and/or alkyl ethers of 5-hydroxymethylfurfural, in the presence of oxygen as an oxidizing gas, a solvent composition comprising a saturated organic acid solvent having from 2 to 6 carbon atoms and water, with a catalyst system comprising cobalt, manganese and bromine.

Step b) of the process of the present invention corresponds to the purification of the crude carboxylic acid composition provided or produced in step a) and results in a purified carboxylic acid composition comprising 2,5-furandicarboxylic acid that is at least partially solid. The process of the present invention comprises at least one purification step selected from the above-defined group, wherein these steps correspond to the most important steps of the most well-established purification methods for crude carboxylic acid compositions that are known in the prior art. Aside from FFCA, other colour bodies and impurities, e.g. so called heavy furanics, i.e. molecules that comprise more than one furan moiety, are also oftentimes removed during the purification step.

Hydrogenating at least a portion of the 5-formyl-2-furancarboxylic acid corresponds to a purification by hydrogenation that is based on the well-known principle that several impurities in the crude carboxylic acid composition can be selectively hydrogenated and then separated from the FDCA.

Within the framework of the present invention, purification by hydrogenation is especially preferred, wherein the hydrogenation is preferably conducted by contacting the crude carboxylic acid composition with hydrogen in the presence of a hydrogenation solvent and a hydrogenation catalyst to hydrogenate FFCA to hydrogenation products and separating the FDCA from the hydrogenation products wherein the hydrogenation solvent is preferably water and the hydrogenation catalyst is preferably palladium on carbon. As a general principle, the hydrogenation catalyst may be selected from a wide variety of available catalysts. Typically, the hydrogenation catalyst comprises one or more metals or metal compounds selected from the metals in the Groups 8 to 10 of the Periodic Table of Elements on a carrier. Such suitable metals include Pt, Pd, Ru, Rh, Ir, Os, Ni, Co and mixtures thereof. As is known in the art, such hydrogenation processes usually take place under fully dissolved conditions.

The step of oxidizing at least a portion of the 5-formyl-2-furancarboxylic acid corresponds to purification by post oxidation and is based on the concept, that the product of incomplete oxidation, i.e. FFCA, can be oxidized to FDCA in a subsequent oxidation reaction.

The purification by recrystallization of at least a portion of the FDCA corresponds to the well-known technique of dissolving the carboxylic acid product in a second solvent and/or changing the solubility of FDCA in the original solvent by changing the temperature in order to dissolve and subsequently precipitate the desired product.

Finally, the step of hydrolysing of dialkyl ester of 2,5-furandicarboxylic acid corresponds to purification processes in which the FDCA and/or mono alkyl esters of FDCA in the crude carboxylic acid composition is esterified with an alcohol to yield the dialkyl ester of 2,5-furandicarboxylic acid (e.g. FDCA-DMe), wherein the purification is achieved by distillation, recrystallization, or melt crystallization of the resulting composition and by subsequently hydrolysing the purified dialkyl esters of FDCA to obtain the purified FDCA. In other words, the step of hydrolysing of dialkyl ester of 2,5-furandicarboxylic acid corresponds to forming a dialkyl ester of FDCA from the crude carboxylic acid composition, purifying the dialkyl ester of FDCA, and then hydrolysing the dialkyl ester of FDCA to obtain FDCA.

In step c) a treatment solvent composition is provided or produced that comprises more than 95% by weight of water, with respect to the weight of the treatment solvent composition. The treatment solvent composition is the solvent composition that serves as a solvent during the thermal treatment step and as a carrier liquid in a dispersion for the remaining solid. Preferred treatment solvent compositions comprise a saturated organic acid having 2 to 6 carbon atoms and water.

It was surprisingly found that acceptable results can be obtained when the treatment solvent composition comprises water as the dominant component, i.e. more than 95% by weight of water with respect to the weight of the treatment solvent composition. As the usage of water is comparably cheap and allows for a very sustainable process, the usage of essentially pure water as a treatment solvent composition is preferred.

The treatment solvent composition can be provided, e.g. by mixing of water with other solvents in a different reactor and feeding it to the process of the present invention. However, the treatment solvent composition can also be produced within the framework of the process of the present invention. Therein, it is particularly preferred to use the solvent composition employed in the purification step b) for producing the treatment solvent composition. The production of treatment solvent composition from the solvent that is used in the purification step b) can comprise all suitable duration of the thermal treatment, provided that the actual value is within the defined range for at least 5 min.

The skilled person can adjust the thermal treatment conditions to the required degree of dissolution, wherein the following table can be used that lists values for the solubility of FDCA at a given temperature depending on the solvent composition employed. These data were developed from experimental values and fit to an appropriate solubility model. Intermediate values can be obtained by interpolation.

| Solubility of FDCA for a given temperature and solvent in wt % | | | | | | | |
|---|---|---|---|---|---|---|---|
| Solvent comp, by weight HAc:Water | 140° C. | 150° C. | 160° C. | 170° C. | 180° C. | 190° C. | 200° C. |
| 95:5 | 3.3 | 4.4 | 5.7 | 7.3 | 9.3 | 11.6 | 14.3 |
| 90:10 | 3.5 | 4.5 | 5.6 | 7.0 | 8.7 | 10.6 | 12.8 |
| 80:20 | 4.9 | 6.1 | 7.5 | 9.1 | 10.9 | 12.9 | 15.1 |
| 70:30 | 6.8 | 8.3 | 10.0 | 12.0 | 14.2 | 16.6 | 19.2 |
| 60:40 | 8.2 | 10.0 | 12.1 | 14.5 | 17.0 | 19.9 | 22.9 |
| 50:50 | 9.0 | 11.0 | 13.4 | 16.0 | 19.0 | 22.1 | 25.6 |
| 40:60 | 9.1 | 11.3 | 13.9 | 16.7 | 19.9 | 23.4 | 27.1 |
| 30:70 | 8.9 | 11.1 | 13.8 | 16.8 | 20.1 | 23.8 | 27.8 |
| 20:80 | 8.3 | 10.6 | 13.3 | 16.3 | 19.8 | 23.7 | 27.8 |
| 10:90 | 7.7 | 9.9 | 12.6 | 15.6 | 19.2 | 23.1 | 27.4 |
| 0:100 | 7.0 | 9.2 | 11.7 | 14.8 | 18.4 | 22.4 | 26.8 | steps for arriving at the treatment solvent composition as defined above, including filtration, addition of organic acid solvent having from 2 to 6 carbon atoms, addition of water, removal of organic acid compounds or removal of water.

In a preferred embodiment, the purified carboxylic acid composition obtained in step b) and at least a portion of the solvent used for purification in step b) are both routed to a thermal treatment reactor, wherein preferably saturated organic acid solvent having from 2 to 6 carbon atoms and/or water is either added as additional solvent or removed for producing the thermal treatment composition. The said portion of the solvent, for example, could consist of solvent which remains adhered to the solid after a step of filtration or centrifugation.

Step d) comprises providing or producing a thermal treatment composition comprising the purified carboxylic acid composition and the treatment solvent composition. The thermal treatment composition will in practice comprise a liquid phase and a solid phase. The purified carboxylic acid composition is obtained from step b). The treatment solvent composition is from step c). The thermal treatment composition can be obtained by combining the purified carboxylic acid composition and the treatment solvent composition in any way known to be suitable to the person skilled in the art.

In the context of the present invention, step e) is oftentimes called thermal treatment or thermal treatment step.

According to the invention, the thermal treatment composition is subjected to elevated temperatures in the range of 140 to 200° C. for a time in the range of 5 to 240 minutes. It is essential for the present invention that the percentage of dissolved FDCA, relative to the total amount of FDCA is in the range of 10 to 80%. It is preferred that this degree of dissolution is maintained for at least 5 min during the overall thermal treatment, wherein it is preferred that the respective amount of dissolved FDCA is within the given range during the entire 5 to 240 minutes of thermal treatment. It is preferred that the percentage of dissolved 2,5-furandicarboxylic acid is in the given range when averaged over the After the thermal treatment composition is subjected to elevated temperatures in the thermal treatment step e), the treated composition is cooled down to a temperature in the range of 20 to 80° C., thereby decreasing the solubility of FDCA in the solvent, leading to precipitation of the carboxylic acid composition. At least a portion of the solid FDCA is separated from the treated composition to obtain carboxylic acid composition wherein a mother liquor remains that comprises water.

The carboxylic acid composition not only exhibits an increased purity compared to the purified carboxylic acid composition but also features solid particles that, unlike in the purified carboxylic acid composition, tend not to exhibit an unfavourable plate-like shape but tend to be more spherical. Likewise, the distribution of particle sizes tends to be more favourable which allows for a more convenient handling of the solid product. The resulting carboxylic acid composition tends to exhibit very beneficial mixing behaviour with alkylene glycol, preferably ethylene glycol, and therefore constitutes a very promising starting material for the production of polyalkylenefuranoate.

The above-described thermal treatment step that is used in the process of the present invention can beneficially be incorporated into existing processes for producing carboxylic acid compositions comprising FDCA as the process of the invention is not limited with respect to the technology that is used for obtaining crude FDCA and can be combined with the most relevant purification processes known in the prior art.

It is beneficial that the treatment solvent composition comprises water, as water is among the most common solvents used in several processes of the prior art for both the oxidation reaction and the purification of crude FDCA, e.g. during hydrogenation or post oxidation of impurities. This allows for an efficient plant management and reduces the need for storing additional chemical substances, therefore reducing storage costs.

Surprisingly, with the process of the present invention it is possible to obtain the above-describes beneficial effects without the need for expensive catalysts or highly corrosive and/or hazardous substances, wherein the surprisingly high suitability of water as a major component of the treatment solvent composition is particular beneficial. Furthermore, it is possible to reuse the treatment mother liquor that comprises water for use in other steps of the process according to the invention, preferably in the oxidation step and/or the purification step and/or the thermal treatment step. This allows to arrive at a particular sustainable process with low waste generation.

Preferred is a process that in step b) comprises at least two steps selected from the group defined in step b). Also preferred is a process according to the invention, wherein in step b) the purifying comprises the step of hydrogenating at least a portion of the 5-formyl-2-furancarboxylic acid and the step of crystallizing at least a portion of the solid 2,5-furandicarboxylic acid from the hydrogenation reaction mixture.

Within the framework of the present invention, the expression "at least a portion of" preferably means at least 20%, preferably at least 30%, more preferably at least 40%, even more preferred at least 50%, most preferred at least 60%, wherein for concentrations these values are given as percent by weight if not indicated otherwise.

Preferred is a process according to the invention, wherein the crude carboxylic acid composition and/or the purified carboxylic acid composition comprise mono alkyl ester of 2,5-furandicarboxylic acid, preferably mono methyl ester of 2,5-furandicarboxylic acid (FDCA-Me).

As discussed before, the preferred process is particularly beneficial due to the fact, that the problem underlying the present invention was found to be especially pronounced for those processes that comprise mono alkyl ester of FDCA in the crude carboxylic acid composition and/or the purified carboxylic acid composition. A respective crude carboxylic acid composition comprising mono alkyl ester of FDCA can for example be produced by oxidizing a feed of starting materials that comprise an alkyl ether of 5-HMF. Due to the fact that most of the prior art purification methods are less suitable for completely removing mono alkyl esters of FDCA from a crude carboxylic acid composition, it is often observed that both the crude carboxylic acid composition and the purified carboxylic acid composition comprise mono alkyl ester of 2,5-furandicarboxylic acid.

In one of the most mature technologies in the field, mono methyl ester of FDCA and mono ethyl ester of FDCA are the most relevant mono alkyl esters of FDCA, wherein the mono methyl ester of FDCA is particularly prevalent, so that the presence of monomethyl ester of FDCA (FDCA-Me) in the crude carboxylic acid composition and the purified carboxylic acid composition is particularly preferred, due to its high industrial relevance. As set out in detail above, the mechanical and physical properties of solid purified FDCA are oftentimes found to be less desirable when the purified FDCA also comprises mono alkyl ester of FDCA, in particular monomethyl ester of FDCA. Without wishing to be bound by any theory, it is believed that this is due to the formation of a so-called solid solution of FDCA and FDCA-Me. Surprisingly, the inventors of the present invention found that the solid solution of FDCA and FDCA-Me can be compensated and/or prevented very efficiently with the process of the present invention that proves to be particularly effective both with respect to the removal of FDCA-Me as well as with respect to the enhancement of physical and mechanical properties of the solid product.

Preferred is a process according to the invention, wherein step e) is conducted in a reactor that is pressurized with an inert gas, preferably nitrogen or argon, and/or wherein the thermal treatment composition in step e) is agitated for at least a portion of the time, preferably by stirring, to expose the solid 2,5-furandicarboxylic acid to shear forces.

It is particular beneficial to conduct step e) in a reactor that is pressurized with an inert gas as this reduces the presence of oxygen or other reactive gaseous compounds in the reactor, that could otherwise be present from preceding process steps. In these embodiments, the atmosphere in the reactor during operation is predominantly made up by the inert gas and the vaporized organic acid solvent and/or water. As a consequence, undesired side reactions of FDCA with reactive gaseous compounds are inhibited. Therefore, the usage of an inert gas allows for a particularly safe process, as the likelihood of potentially dangerous side reactions and/or exothermic reactions and/or fires is decreased.

While the result of the process according to the invention is oftentimes found to be satisfactory with the thermal treatment of the thermal treatment composition alone, we discovered that the beneficial influence on the mechanical and physical properties of the obtained particles of the carboxylic acid composition can be further increased, when the thermal treatment composition in step e) is also agitated, in order to expose the solid FDCA particles to shear forces. Without wishing to be bound to any theory, it is believed that the agitation of the thermal treatment composition during the thermal treatment also enhances the homogeneity of the liquid phase and reduces concentration gradients of impurities, thereby facilitating both the purification and the improvement of the mechanical properties of the resulting particles. The agitation can be provided with all suitable means that are known to the skilled person, e.g. by stirring of the thermal treatment composition or utilizing an external pumping loop.

Preferred is a process according to the invention, wherein the thermal treatment composition comprises 2,5-furandicarboxylic acid in an amount of 15 to 45%, preferably 20 to 40%, by weight with respect to the weight of the thermal treatment solvent composition.

Such a preferred process is beneficial, as the desired ratio between dissolved and solid FDCA in step e) can readily be obtained when the respective amounts of FDCA are used without the need for high temperatures and with a high flexibility with respect to the composition of the solvent employed.

Preferred is a process according to the invention, wherein the treatment solvent composition comprises acetic acid, preferably in an amount in the range of 0.05 to 4.5%, preferably 0.1 to 3%, by weight with respect to the weight of the treatment solvent composition.

Respective treatment solvent compositions with the defined amounts of acetic acid particularly preferred, if the main objective is to obtain the highest possible degree of purity and the most beneficial mechanical properties. The presence of acetic acid was found to provide for the best impurity removal.

As discussed before, the usage of water as major component of the treatment solvent composition surprisingly yields reasonable results in the thermal treatment and can be favourable from a cost and sustainability perspective. In particular, thermal treatment in water was found to yield similar particle shapes as thermal treatment in organic acid, that was sometimes found to produce better results with respect to impurity removal but has other disadvantages, e.g. with respect to the sustainability of the process and costs of starting materials. Furthermore, thermal treatment in water at least has the potential to lead to a similar product quality with respect to FDCA-Me and FCA content if the process parameters are adjusted (e.g. longer residence times). Without wishing to be bound to any theory, it is believed that at least part of this could be due to the conversion of FDCA-Me to FDCA by hydrolysis. It was found that a thermal treatment that employs predominantly water or only water as solvent sometimes requires higher temperatures, or longer residence times compared to thermal treatment in organic acids. Correspondingly, processes are preferred, wherein the thermal treatment composition in step e) is subjected to elevate temperatures in a range of 160 to 200° C. for a time in the range of 30 to 240 min.

Preferred is a process according to the invention, wherein the purified carboxylic acid composition produced in step b) comprises less than 25%, preferably less than 15%, most preferred less than 10%, by weight of solvent with respect to the weight of the purified carboxylic acid composition.

The respective process is preferred, because it can be beneficial to remove a significant amount of the solvent that was used during the purification step b), from the purified carboxylic acid composition before mixing it with the treatment solvent composition to obtain the thermal treatment composition (e.g. in order to keep water from the purification step out of the solvent loop for thermal treatment that shall be conducted at low water contents). The respective process is particularly beneficial for processes that employ purification methods that use different solvents that could be unfavourable for the thermal treatment step, e.g. aromatic compounds, or processes that produce large amounts of soluble by-products and/or impurities that can be removed before thermal treatment by the intermediate isolation of the purified carboxylic acid.

Preferred is a process according to the invention, wherein the process parameters in steps e) and f) are selected to produce particles of 2,5-furandicarboxylic acid that
  exhibit less than 35%, preferably less than 25%, decrease in the mean particle diameter between particle size measurements at 0.2 bar and 2 bar dispersion pressure, and/or
  have a volume averaged median particle size (d50) in the range of 50 to 300 µm, preferably in the range of 60 to 200 µm.

One of the most beneficial aspects of the process of the present invention is that it can provide both for an additional purification and an enhancement of the mechanical and physical properties of the obtained product. Such synergistic relationship surprisingly allows to reliably estimate or predict either the aspect of purity or the aspect of mechanical properties by measuring and analyzing the respective other parameter. As the mechanical properties and/or the particles size distribution of the product obtained in the process according to the invention in most cases can be easily be determined, the preferred process is particularly advantageous, as the skilled person can monitor the above parameters and can quite reliably predict, when the desired degree of purity is reached, without the need to conduct a comprehensive chemical analysis of the product. The respective advantage was found to be particularly distinct for processes that comprise mono alkyl esters of FDCA. Without wishing to be bound by theory, it is believed that this is caused by the undesirable effect that the mono alkyl ester of FDCA in several cases has on the mechanical properties and the particle size distribution of the obtained product. In other words, the desired particle shape as defined in the preferred process was oftentimes found to be reached when also the desired degree of purity with respect to FDCA-Me had been obtained.

Both the mean particle diameter and the volume average median particle size (d50) are parameters that are well known to the skilled person and that can reliably be determined. In practice the typical measurements used in the art for determination of the respective parameters are expected to yield at least similar values. Therefore, for the overwhelming majority of cases the equipment used for determination of the mean particle diameter and volume average median particle size (d50) is not crucial. However, in case of doubt, the mean particle diameter and volume average medium particle size (d50) is measured using one of the most common devices for particle size measurements, i.e. a laser diffraction particle size analyzer model Mastersizer 3000, manufactured by Malvern Panalytical using the PSD dry method with a setting of the laser obscuration of 1.5% and a value of 1.538 of the refractive index and a dispersing pressure of 0.2 bar.

The decrease in mean particle diameter between particle size measurements at 0.2 bar and 2 bar dispersion pressure is measured for the same substance but on different aliquots (i.e. not subsequent measurements on the same particles). For this the sample is tested using two different levels of air pressure to create particle dispersion. The results using a dispersion pressure of 0.2 bar are considered to be the "gentlest" while using a dispersion pressure of 2 bar is a more aggressive dispersion. This can be used as a test of particle strength and stability under conditions, for example, which might represent the stress experienced during a pneumatic conveying operation.

Preferred is a process according to the invention wherein the crude carboxylic acid composition comprises 2-furancarboxylic acid, preferably in an amount in the range of 1 to 2000 ppm by weight with respect to the weight of the composition, more preferably in an amount in the range of 1 to 1000 ppm by weight with respect to the weight of the composition and wherein the carboxylic acid composition preferably comprises 2-furan carboxylic acid in an amount of not more than 700 ppm by weight, more preferably in an amount of not more than 500 ppm by weight.

As discussed above, FCA is among those impurities in crude carboxylic acid compositions comprising FDCA, that are oftentimes insufficiently removed by prior art purification processes. In particular, FCA is an aromatic carboxylic acid and is rather stable under oxidizing conditions, making it difficult to remove by oxidization. Further, as an aromatic carboxylic acid it is also resistant to hydrogenation under conditions which hydrogenate FFCA but not FDCA, making it difficult to remove by hydrogenation. Also, although it can be removed by esterification of FDCA to form the diester, followed by distillation, recrystallization or melt crystallization, new FCA is formed when that purified dialkyl ester is hydrolyzed to produce the diacid and so this method is also not appropriate for removal of FCA. Surprisingly, it was found that the process of the present invention, i.e. the process that comprises the thermal treatment, is able to significantly reduce the amount of FCA in the carboxylic acid composition. Due to the surprisingly high suitability for removing FCA from carboxylic acid compositions comprising FDCA, the preferred process is particularly advantageous. As discussed with respect to the mechanical and physical properties before, it was found that for carboxylic acid compositions that comprise FCA, when using a thermal treatment, it is surprisingly possible to quite reliably estimate or predict from the concentration of FCA in the carboxylic acid composition, whether the mechanical and physical properties of the product are likely to be sufficient as well. Carboxylic acid compositions that after thermal treatment comprise FCA in an amount of no more than 700 ppm, preferably 500 ppm, by weight with respect to the weight of the carboxylic acid composition were found to exhibit satisfactory physical and mechanical properties. This is beneficial, as depending on the equipment available in the facility it can be preferred to analyse the chemical composition instead of directly analysing the mechanical properties of the obtained product.

Preferred is a process wherein the crude carboxylic acid composition comprises 2,5-furandicarboxylic acid in an amount in the range of 90 to 99.5%, preferably in an amount in the range of 94 to 99%, by weight with respect to the weight of the crude carboxylic acid composition,
and/or
wherein the crude carboxylic acid composition comprises 2,5-furandicarboxylic acid in an amount in the range of 90 to 99.5%, preferably in an amount in the range of 94 to 99%, by weight with respect to the total weight of all furanics in the crude carboxylic acid composition,
and/or
wherein the crude carboxylic acid composition comprises 5-formyl-2-furancarboxylic acid in an amount in the range of 100 to 3800 ppm, preferably in an amount in the range of 150 to 3000 ppm, and more preferably in an amount of not more than 1500 ppm by weight with respect to the weight of the crude carboxylic acid composition,
and/or
wherein the crude carboxylic acid composition comprises mono alkyl ester of 2,5-furandicarboxylic acid in an amount in the range of 0.2 to 5.0%, preferably in an amount in the range of 0.3 to 3%, by weight with respect to the weight of the crude carboxylic acid composition.

The above process is preferred as the thermal treatment conducted in such process was found to be particular effective when employed in processes that started with the respective crude carboxylic acid compositions. The term furanics is known in the art and describes all compounds that comprise at least one furan moiety, i.e. a substituted or unsubstituted furan ring. In practice, the most relevant furanics typically are furan, 5-HMF and its ethers and esters, FCA and its esters, FDCA and its esters, FFCA and its esters, 2,5-Diformylfuran, 5-methylfuran-2-carboxylic acid, and dimers of these compounds.

Preferred is a process according to the invention, wherein the purifying in step b) comprises the step of hydrogenating at least a portion of the 5-formyl-2-furancarboxylic acid,
and/or
wherein the purifying in step b) also comprises a step of isolating the purified carboxylic acid composition, wherein the isolating comprises filtering and/or washing and/or drying.

The respective process is preferred because the thermal treatment was found to show especially good results when combined with hydrogenation as a purification method. Not only is the purification by hydrogenation particularly cost efficient and suitable for large volumes of product that are handled in continuous or semi-continuous processes, it also is very efficient at removing FFCA from the crude carboxylic acid composition. Hydrogenation as purification method is also particularly preferred as this process usually employs a hydrogenation solvent comprising predominantly water. Therefore, the hydrogenation solvent composition can oftentimes be used as a precursor for the treatment solvent composition that is employed during thermal treatment. While in most cases it will be required to add water and/or organic acids to adjust the desired composition of the treatment solvent composition, in some cases it is possible to directly use at least a portion of the hydrogenation solvent as treatment solvent composition without modifications. However, in these cases it is oftentimes preferred to remove at least a portion of the hydrogenation solvent, in order to establish the desired percentage of dissolved FDCA during thermal treatment. For example, a process of hydrogenation utilizing fully dissolved conditions could then be crystallized using an evaporative crystallizer, to remove a portion of the hydrogenation solvent and increase the concentration of FDCA in the process. Other options for partial solvent removal include processes such as decantation, hydrocyclones or clarifiers.

While the process of the present invention reliably yields good results with respect to the purity and the mechanical properties of the carboxylic acid composition, it was found that it can be particular beneficial, to include an isolation step, in that the purified carboxylic acid composition is isolated from other components, e.g. the solvent used for purification. Such an isolation step typically comprises the steps of filtering and/or washing and/or drying. While respective processes are usually not optimized with respect to cost and/or time efficiency, the intermediate isolation of the solid product facilitates the purification during the thermal treatment, allowing close control of the composition of the thermal treatment composition, without need to account for the variation in the liquid components. Correspondingly and as described above, respective processes are expected to yield among the highest purity for the carboxylic acid composition.

Preferred is a process according to the invention, wherein the purified carboxylic acid composition comprises 2,5-furandicarboxylic acid in an amount in the range of 95 to 99.9%, preferably in an amount in the range of 98 to 99.9%, by weight with respect to the weight of the purified carboxylic acid composition,
and/or
wherein the purified carboxylic acid composition comprises 5-formyl-2-furancarboxylic acid in an amount in the range of 1 to 200 ppm, preferably in an amount in the range of 1 to 100 ppm, by weight with respect to the weight of the purified carboxylic acid composition,
and/or
wherein the purified carboxylic acid composition comprises mono alkyl ester of 2,5-furandicarboxylic acid in an amount in the range of 100 to 13000 ppm, preferably in an amount in the range of 200 to 11000 ppm, by weight with respect to the weight of the purified carboxylic acid composition
and/or
wherein the purified carboxylic acid composition comprises 2-furan carboxylic acid in an amount in the range of 1 to 2500 ppm, preferably in an amount in the range of 1 to 1700 ppm, by weight with respect to the weight of the purified carboxylic acid composition.

The respective process is preferred, as the thermal treatment of the process of the present invention was found to work particularly well with purified carboxylic acid compositions of the given specification. While the process of the present invention tends to provide for an increased degree of purity and enhanced mechanical and physical properties of the product for a broad variety of purified carboxylic acid compositions that were studied, it was sometimes observed that the efficiency decreased when the overall amount of impurities, in particular the amount of alkyl esters of FDCA and FCA exceeds certain thresholds. Similar effects were observed other purification methods due to the fact that the amount of solvent that can be employed to dissolve the impurities is limited by the essential feature of the thermal treatment namely that a specific amount of FDCA needs to remain in the solid phase during thermal treatment.

Likewise, the above process is preferred, as the thermal treatment of the present invention was found to be less suitable for removing FFCA that is also an undesired chain terminator in polymer grade FDCA. Correspondingly, processes are preferred in that the purification step b) is conducted in a way to remove most of the FFCA before the thermal treatment. Knowing about the comparably low capability of the thermal treatment to remove FFCA, the skilled person is able to adjust the prior art purification methods without problems to yield purified carboxylic acid composition with the desired FFCA amounts.

Preferred is a process wherein the temperature in step e) is in the range of 150 to 190° C., preferably in the range of 160 to 190° C.,
and/or
wherein the thermal treatment composition in step e) is subjected to an elevated temperature for a time in the range of 15 to 120 min, preferably in the range of 30 to 90 min, most preferably to a time in the range of 0.7*(220−T/° C.) to 3.0*(220−T/° C.) min, wherein T is the temperature in step e),
and/or
wherein in step e) the percentage of dissolved 2,5-furandicarboxylic acid, relative to the total amount of 2,5-furandicarboxylic acid, is in the range of 20 to 60%, preferably in the range of 30 to 60%.

The above process is preferred as it defines those process parameters of the thermal treatment, that were found to be most suitable for obtaining the best results for the carboxylic acid composition with respect to both purity and mechanical properties. Therein, the temperature ranges during thermal treatment and the percentage of dissolved FDCA are related by a factor that is mostly determined by the composition and amount of treatment solvent composition. Conveniently, based on screening experiments, suitable residence times can be given in dependency of the thermal treatment temperature as disclosed above.

Preferred is a process according to the invention, wherein the treated composition in step f) is cooled to a temperature in the range of 30 to 80° C., preferably in the range of 40 to 80° C.,
and/or
wherein step f) comprises the step of treating the treatment mother liquor to remove at least a portion of the water from the residual treated composition,
and/or
wherein step f) comprises the step of recycling at least a portion of the treatment mother liquor for providing the treatment solvent composition in step c).

As a decrease in temperature reduces the solubility of FDCA in the treatment solvent composition which can lead to precipitation of dissolved FDCA, it can be understood that the cooling in step f) is expected to have an impact on the mechanical properties of the obtained product. Correspondingly, the skilled person that intends to modify the mechanical properties of the carboxylic acid composition should contemplate changing the temperature gradient between thermal treatment in step e) and cooling in step f). It was found that it can be beneficial, if the temperature gradient during step f) is reproducibly controlled and not too steep. It is preferred to cool the treated composition to a temperature, that is still well above the typical room temperature of 20 to 25° C. A cooling rate of up to 600 K/hour is very acceptable, but levels of 30 to 120 K/hour are preferred. While not wishing to be bound by theory, we believe that the presence of a large solids fraction at the processing temperature reduces the risk of fines formation or spontaneous nucleation which might otherwise be experienced at these relatively high cooling rates. A high cooling rate is advantageous by not prolonged the thermal stress to the system for any longer than necessary to provide the desired treatment effect. Excess thermal stress can lead to unwanted reactions, including, for example, formation of colour. The high cooling rate is advantageously provided by evaporating at least a portion of the solvent, e.g. by allowing the solvent to boil.

To increase the sustainability of the thermal treatment step and to reduce the amount of waste generated by the process according to the invention, it is preferred to recycle at least a portion of the treatment mother liquor back to the thermal treatment step. This means that at least a portion of the treatment mother liquor is used as treatment solvent composition in the thermal treatment of purified carboxylic acid composition. In this recycle process it can be important to adjust the solvent composition for any changes which have occurred. For example, if the purified carboxylic acid composition is water wet, for example being filtered and water washed but not dried, then that water will be incorporated into the mother liquor after the thermal treatment and at least a portion should be removed from the mother liquor before recycling. In this manner the overall thermal treatment composition can be maintained at the desired concentration levels.

Furthermore, the invention relates to a carboxylic acid composition comprising greater than 98% by weight of 2,5-furandicarboxylic acid with respect to the weight of the carboxylic acid composition and which carboxylic acid composition particles exhibit less than 35% decrease in the mean particle diameter between particle size measurements at 0.2 bar and 2 bar dispersion pressure, wherein the carboxylic acid composition preferably comprises less than 0.1% by weight of a saturated organic acid solvent having from 2 to 6 carbon atoms and wherein the carboxylic acid composition is preferably produced using the process of the present invention.

Faced with the objective of providing a carboxylic acid composition that has good physical and/or mechanical properties and that can be efficiently processed e.g. during storage or shipping of the product, we surprisingly found that the technical problem can be solved by providing the above carboxylic acid composition. The respective parameter is an indication that particles are suitable for efficient handling and long-time storage and are therefore beneficial.

Carboxylic acid compositions of the present invention can be produced using the process of the present invention, in particular by the step of thermal treatment of a purified carboxylic acid composition. Correspondingly, a carboxylic acid composition is preferred that was produced using the process of the present invention or a preferred embodiment of the process of the present invention.

Preferred is a carboxylic acid composition according to the invention, wherein the carboxylic acid composition particles have a volume averaged median particle size (d50) in the range of 50 to 300 μm, preferably in the range of 60 to 200 μm,
and/or
wherein the carboxylic acid composition particles have a d10 of 20 μm or greater, wherein d10 is defined as the diameter at which 10% of particles by volume have a smaller diameter,
and/or
wherein the carboxylic acid composition particles have a d90 of 400 μm or less, wherein d90 is defined as the diameter at which 90% of particles by volume have a smaller diameter,
and/or
wherein the ratio of d50 to d10 is in the range of 1 to 3, preferably in the range of 1.5 to 2.5.

Upon analysis of those carboxylic acid composition particles that exhibited the most beneficial mechanical properties, it was found that the respective carboxylic acid composition particles tend to exhibit a specific distribution of particle sizes that is believed to at least contribute to the fact that carboxylic acid composition particles according to the invention can easily be poured and pumped through pipelines, while maintaining these properties even after extended times of storage. Furthermore, these carboxylic acid composition particles were found to have properties which were favorable for making slurries with good stability and good pumping and mixing characteristics.

Preferred is a carboxylic acid composition according to the invention, wherein the carboxylic acid composition comprises mono alkyl ester of 2,5-furandicarboxylic acid, preferably mono methyl ester of 2,5-furandicarboxylic acid, in an amount in the range of 200 to 5000 ppm by weight with respect to the weight of the carboxylic acid composition, and/or
wherein the carboxylic acid composition comprises 2-furancarboxylic acid in an amount in the range of 10 to 500 ppm, preferably 20 to 200 ppm, by weight with respect to the carboxylic acid composition,
and/or
wherein the carboxylic acid composition comprises 5-formyl-2-furancarboxylic acid in an amount in the range of 1 to 100 ppm, preferably 2 to 50 ppm, most preferred less than 30 ppm, by weight with respect to the carboxylic acid composition. Such carboxylic acid composition is preferred, as not only the mechanical parameters are particularly favorable, but the composition also comprises low amounts of those impurities, that are known to have the most detrimental effect on the polymerization behavior of the carboxylic acid composition.

The invention also relates to a starting material for the production of polyalkylenefuranoate, also called poly(alkylene-2,5-furandicarboxylate), comprising the carboxylic acid composition according to the invention and alkylene glycol, preferably ethylene glycol, and a polymerization catalyst, wherein the polyalkylenefuranoate preferably is poly(ethylene-2,5-furandicarboxylate).

The respective starting material for the production of polyalkylenefuranoate is a mixture of the carboxylic acid composition of the present invention with alkylene glycol and a typical polymerization catalyst known in the art. The respective composition is particularly suitable for use in a polymerization reaction that yields polyalkylenefuranoate. As discussed above, this is attributed to the beneficial mechanical and physical properties of the carboxylic acid composition of the present invention, i.e. the carboxylic acid composition obtained by the process of the present invention. The shape of the FDCA particles and the specific distribution of particle sizes tends to allow for a very efficient mixing with the alkylene glycol, even at low molar ratio. In clear contrast, solid FDCA obtained by prior art purification methods is oftentimes found to not form the desired mixture with ethylene glycol at low molar ratios. This imposes a serious problem on the polymerization process that shall yield a high-performance polymer of a given composition and that therefore cannot easily be adopted to simply increase the molar ratio in order to allow for an enhanced mixing of the starting materials or to provide additional energy required to remove the unwanted extra glycol. In consequence, the carboxylic acid composition of the present invention and its use as starting material in the polymerization of polyalkylenefuranoate is highly beneficial and satisfies a long-felt need, in particular in comparison to purified carboxylic acid compositions that, due to their production history, comprise mono alkyl ester of FDCA.

Hereinafter, the invention is described in more detail using experiments.

Example A—Thermal Treatment

A1—Preparation of Purified FDCA

A crude carboxylic acid composition (cFDCA) comprising 2,5-furandicarboxylic acid and 5-formyl-2-furancarboxylic acid was prepared as described previously according to the teaching of WO 2017/003293 A1. This cFDCA was then subjected to purification by hydrogenation according to the teachings of WO2016195499 and WO2016195500 to produce a purified FDCA, denoted as hFDCA (for hydrogenated FDCA). For understanding the results, it is expedient to analyse the actual composition of the hFDCA.

The hFDCA was analyzed and found to contain >98% by weight of 2,5-furandicarboxylic acid (FDCA), with the main impurities comprising the mono methyl ester of 2,5-furandicarboxylic acid (FDCA-Me), present at 10300 ppm by weight and 2-furancarboxylic acid (FCA), present at 1680 ppm by weight. These levels of impurities are generally considered less suitable for use in polymer production. In particular, the monoester of FDCA would generate methanol during the polymer production which is disadvantageous. The monocarboxylic acid, FCA, has only one polymerization site and is a chain terminator, which limits molecular weight growth. Furthermore, FCA is also implicated in colour formation.

A2—Experimental Setup for Thermal Treatment

The thermal treatment tests were performed in laboratory autoclaves. Heating and cooling was conducted via the walls of the autoclave and an agitator was used.

A3—Comparative Examples 1 and 2—Dissolution of FDCA

Comparative Examples 1 and 2 use 10 wt % hFDCA in water, and were heated during thermal treatment to 160° C. in order to fully dissolve the FDCA (the low amount of hFDCA is required to enable complete dissolution). This complete dissolution is not according to the invention. The thermal treatment composition was then held for 30 minutes at the given temperature. In Comparative Example 1 the sample was subsequently cooled to 40° C. by rapid cooling. In Comparative Example 2 the sample was first cooled to 109° C. in 15 min by the evaporation of water using depressurization and subsequently cooled to 40° C. by rapid cooling. In each case the samples were then filtered at 40° C. under vacuum, washed with water (1:1 by weight, compared to dry solid), and subsequently dried.

As shown in the table below, the treatment resulted in a reasonable decrease in the monoester content of the dried FDCA, but the FCA content actually increased relative to the initial feed (indicating additional decarboxylation of FDCA/FDCA-Me when processed in water).

Figure 1:
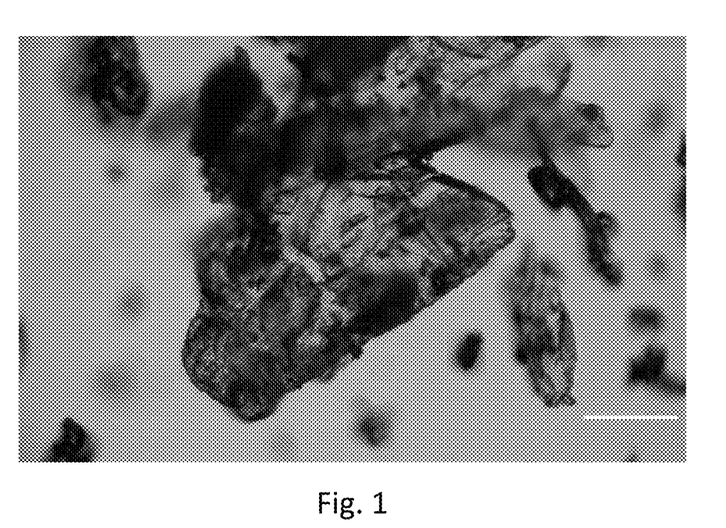
FIG. 1: Exemplary particles of FDCA obtained in a process without thermal treatment according to the invention, wherein the scale corresponds to 100 μm.
Figure 2:
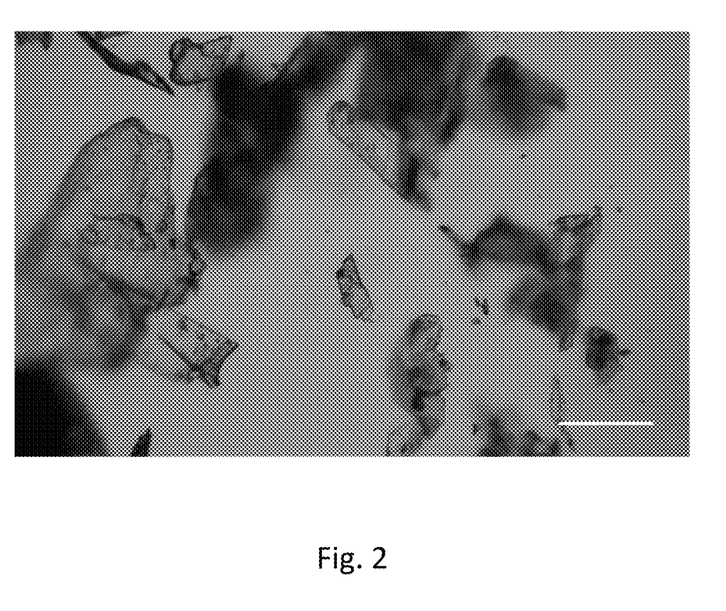
FIG. 2: Exemplary particles of FDCA obtained in a process without thermal treatment according to the invention, wherein the scale corresponds to 100 μm.

Microscope photos revealed that the obtained particles after thermal treatment have the appearance of "broken glass" with rather flat plates, with sharp edges, and significant levels of fines. This particle shape is considered unfavourable. Exemplary photos of the particles obtained in Comp 1 and Comp 2 are shown in FIGS. 1 and 2, respectively. The photos were obtained using a Euromex iScope IS.1053-PLPOLRi microscope with 20× magnification.

TABLE 1

| Comparative Example 1 and 2 | | | | | | |
|---|---|---|---|---|---|---|
| Test | Solvent mix (HAc:Water) | hFDCA (wt %) | T (° C.) | % hFDCA dissolved | FCA, dry cake (ppm) | FDCA-Me, dry cake (ppm) |
| Comp. 1 | 0:100 | 10 | 160 | 100 | 2300 | 4350 |
| Comp. 2 | 0:100 | 10 | 160 | 100 | 3230 | 4260 |

A4—Comparative Examples 3 and 4—Temperature

Comparative Examples 3 and 4 are prepared in a similar way as described above for Comparative Examples 1 and 2, wherein the process parameters are summarized in Table 2 below. In both cases the heating rate was 1.5 K/min to reach the process temperature (i.e. lower than defined in the present invention) that was held for 1 hour, with a subsequent cooling to 40° C. at 1 K/min.

For a better understanding, the estimated FDCA solubility in the given solvent at the process temperature is provided as well.

As shown in Table 2 below, the thermal treatment with incomplete dissolution at lower temperatures resulted in a reasonable decrease in both the monoester and FCA content of the dried FDCA. However, while the removal efficiency for FCA is increased, the removal efficiency for FDCA-Me is decreased when Comp.4 is compared with Comp.1 and Comp.2. Microscope photos revealed that the obtained particles after thermal treatment have a sharp edged and plate-like appearance. This particle shape is considered unfavourable.

TABLE 2

| Comparative Examples 3 and 4 | | | | | | | |
|---|---|---|---|---|---|---|---|
| Test | Solvent mix (HAc:Water) | hFDCA (wt %) | T (° C.) | Solubility at T, wt % in solvent | % hFDCA dissolved | FCA, dry cake (ppm) | FDCA-Me, dry cake (ppm) |
| Comp. 3 | 70:30 | 24 | 125 | 6.1 | 25 | 820 | 3730 |
| Comp. 4 | 0:100 | 24 | 130 | 5.3 | 22 | 1340 | 5880 |

A5—Examples 1, 2 and 3

Examples 1, 2 and 3 are prepared in a similar way as described above for Comparative Example 1 and Comparative Example 2, wherein the process parameters are summarized in Table 3 below. In all cases the heating rate was 1.5 K/min to reach the process temperature which was maintained for 1 hour, with a subsequent cooling to 40° C. For Examples 1 and 3 the cooling was conducted at a rate of 1 K/min. For Example 2 the sample was first cooled to 107° C. in 7 minutes by evaporation of water using depressurization and subsequently cooled to 40° C. at a rate of 1 K/min.

For a better understanding, the estimated FDCA solubility in the given solvent at the process temperature is provided as well.

Examples 1 and 2 are not considered to be according to the invention and are included for comparison purposes only.

As shown in Table 3 below for Example 3, the thermal treatment according to the invention resulted in a significant decrease in both the FDCA-Me and FCA content of the dried FDCA that is remarkably more pronounced than in Comparative Examples 1 to 4, indicating that both the temperature as well as the correct degree of FDCA dissolution are relevant.

Figure 3:
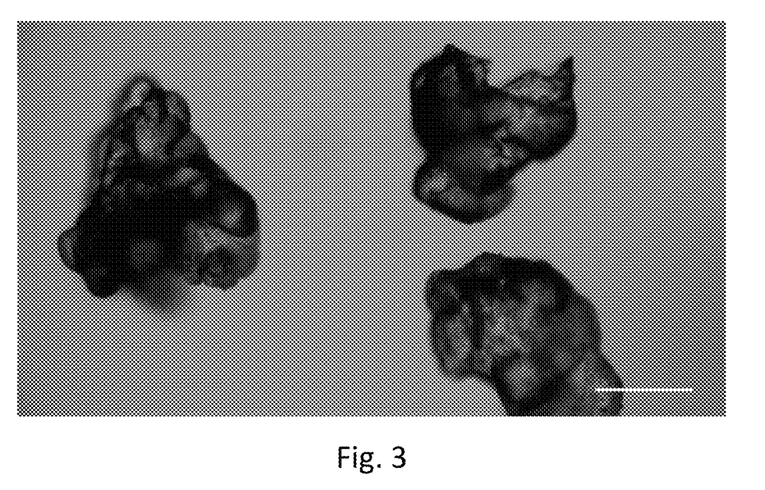
FIG. 3: Exemplary particles of FDCA obtained in a process with thermal treatment according to the invention, wherein the scale corresponds to 100 μm.

Furthermore, microscope photos revealed that the obtained particles after thermal treatment have a rather smooth and rounded shape with a low level of fines. This particle shape is considered very favourable. An exemplary photo of the particles obtained in Example 3 is shown in FIG. 3. The photo was obtained using a Euromex iScope IS.1053-PLPOLRi microscope with 20× magnification.

TABLE 3

Examples 1, 2 and 3

| Test | Solvent mix (HAc:Water) | hFDCA (wt %) | T (° C.) | Solubility at temp., wt % in solvent | % hFDCA dissolved | FCA, dry cake (ppm) | FDCA-Me, dry cake (ppm) |
|---|---|---|---|---|---|---|---|
| Ex. 1 | 70:30 | 30 | 180 | 14.2 | 47 | 440 | 1950 |
| Ex. 2 | 70:30 | 30 | 180 | 14.2 | 47 | 330 | 1180 |
| Ex. 3 | 0:100 | 30 | 180 | 18.4 | 61 | 500 | 1490 |

Example B—Particles

B1—Preparation of Different FDCA Feeds for Use in Thermal Treatment

Mixed furanics, comprising predominantly 5-methoxymethyl furfural (5-HMF ether) and 5-hydroxymethyl furfural (5-HMF), were prepared by the acid catalyzed dehydration of fructose in methanol, followed by partial neutralization of the acid and recovery of the 5-methoxymethyl furfural and 5-hydroxymethyl furfural, according to the teaching of WO 2017/003293 A1.

After recovery, the mixed furanics, were fed to an oxidation reactor along with acetic acid and a catalyst comprising cobalt, manganese, and a source of ionic bromine, according to the teaching of WO 2011/043660 A1. The product of the oxidation was primarily 2,5-furandicarboxylic acid and the monomethyl ester of 2,5-furandicarboxylic acid, along with lesser amounts of 5-formyl-2-furancarboxylic acid and minor amounts of other by-products. This corresponds to a crude carboxylic acid composition that is hereinafter designated as cFDCA. It is noted that the usage of crude cFDCA allows for a particularly good analysis of the impact of the thermal treatment of the invention as the cFDCA has the largest amounts of impurities making the observed effects particular pronounced. Therefore, while the cFDCA was not subjected to a purification step as defined in the process of the invention, the results obtained hereinafter with cFDCA are highly relevant for evaluating the effect of the process of the present invention.

The crude carboxylic acid composition was further purified by various methods.

In one purification process, the diacid was esterified with methanol to form the dimethyl ester of 2,5-furandicarboxylic acid, which was purified and then hydrolyzed in the presence of base and reacidified, to form a purified carboxylic acid composition. The corresponding samples are designated eFDCA.

In another purification process, the crude carboxylic acid composition was purified by mixing it with water and hydrogen, heating to dissolve the solid, and then hydrogenating in a flow system in the presence of a catalyst to form a purified carboxylic acid composition, according to the teachings of WO 2016/195499 A1 and WO 2016/195500 A1. The corresponding samples are designated hFDCA.

Finally, another feed of FDCA was obtained from the hydrogenated FDCA (hFDCA) which was fully dissolved and subsequently recrystallized from water. The corresponding samples are designated rFDCA.

These feeds were analysed and found to contain the levels of FDCA-Me and FCA shown in the table below (ranges indicate the result of several measurements on the same type of sample).

TABLE 4

Crude carboxylic acid

|  | FDCA-ME, ppm | FCA, ppm |
|---|---|---|
| cFDCA | 16000 | 900 |
| eFDCA | 0 | 51 |
| hFDCA | 9140-12200 | 790-1200 |
| rHDCA | 910 | 810 |

B2—Particle Size Analysis

Samples of FDCA, prepared by various methods as described above, were submitted to particle size analysis in order to determine the particle size distribution (PSD) of the sample. The particle size analysis used a laser diffraction particle size analyzer model Mastersizer 3000, manufactured by Malvern Panalytical. The instrument was used to generate a full distribution of the particle sizes, which is then captured in the summary table together with the well-established d10, d50, and d90 parameters, which represent the volume averaged particle size (diameter) cut-offs for 10%, 50% and 90% of the volume of the sample. Further, a statistic is presented to represent the breadth of the particle size distribution, reported as the ratio d50/d10. Large values of this ratio indicate a distribution with a significant population of particles much smaller than the median, or fines, that are found to be unfavourable.

B3—Stress Test

In addition to the standard particle size analysis, the samples were tested using multiple levels of air pressure to create particle dispersion. The results using a dispersion pressure of 0.2 bar are considered to be the "gentlest" while using a dispersion pressure of 2 bar is a more aggressive dispersion. This can be used as a test of particle strength and stability under conditions, for example, which might represent the stress experienced during a pneumatic conveying operation. This test is given quantitatively in the tables below as the reduction in d50 when tested at 2.0 bar compared to 0.2 bar.

B4—Experimental Setup for Thermal Treatment

A 5 liter autoclave made of 316L stainless steel was used for the thermal treatment and the corresponding crystallization. The system is pressure rated to accommodate the temperature and solvents chosen. The vessel was made of 316L stainless steel. Temperature, pressure, and shaft speed are recorded. The impellor is an Ekato "Viscoprop", suitable for this purpose.

B5—Comparative Examples 5 to 12—Particle Size Distribution

For Comparative Examples 5 to 12 the respective material was fully dissolved during thermal treatment and then cooled and crystallized according to the details in the table below. In each case the material was cooled down to 40° C. after being held at the thermal treatment temperature for 30 minutes. Comparative Example 7 used a more sophisticated cooling scheme in that the cooling rate was 20 K/hr to cool from 180° C. to 140° C., then 40 K/hr from 140° C. to 100° C., and then 60 K/hr from 100° C. to 40° C.

The resulting particles were analysed to determine the particle size distribution. The ratio of d50/d10 is used as a measure of the breadth of the distribution, with a large number indicating a significant fraction of particles with a diameter much smaller than the median.

Examples 4 to 9 use lower water concentrations in the treatment solvent composition and are not according to the invention. However, we found the above trends also for treatment solvent compositions that comprise more than 95% by weight of water. Therefore, from the obtained data it can be assumed that a thermal treatment according to the invention will result in a much more favourable particle size distribution with a significant decrease in fines, indicated by the decrease in the d50/d10 ratio.

TABLE 5

Comparative Examples 5 to 12

| Test | Feed | Solvent | FDCA (wt %) | T (° C.) | Cooling Rate (K/hr) | d10 μm | d50 μm | d50/d10 |
|---|---|---|---|---|---|---|---|---|
| Comp. 5 | hFDCA | Water | 20 | 180 | 30 | 38 | 165 | 4.3 |
| Comp. 6 | 2% hFDCA + 8% eFDCA | Water | 10 | 160 | 30 | 53 | 231 | 3.8 |
| Comp. 7 | hFDCA | Water | 20 | 180 | 20/40/60 | 51 | 195 | 3.8 |
| Comp. 8 | hFDCA | Water | 20 | 180 | 60 | 69 | 459 | 6.6 |
| Comp. 9 | hFDCA | HAc:Water 70:30 | 14 | 180 | 30 | 34 | 342 | 10.0 |
| Comp. 10 | cFDCA | HAc:Water 95:5 | 9.3 | 180 | 30 | 81 | 350 | 4.3 |
| Comp. 11 | cFDCA | HAc:water 70:30 | 14 | 180 | 30 | 23 | 314 | 13.6 |
| Comp. 12 | cFDCA | Water | 9.2 | 150 | 30 | 12 | 100 | 8.3 |

B6—Examples 4 to 9—Particle Size Distribution

Thermal treatment for Examples 4 to 9 was conducted in a similar way as described above for Comparative Examples 5 to 12, wherein the process parameters are summarized in Table 6 below. In Examples 8 and 9 the thermal treatment time was increased to 240 min.

B7—Comparative Examples 13 and 14—Particle Strength

Comparative Examples 13 and 14 were subjected to thermal treatment by taking a sample of FDCA which had been purified by hydrogenation (hFDCA) and subjecting it to a full dissolution and controlled crystallization, according to the conditions in the table below. In each case the sample

TABLE 6

Examples 4 to 9

| Test | Feed | Solvent | Wt % FDCA | T ° C. Holding time | Cooling Rate (K/hr) | d10 μm | d50 μm | d50/d10 |
|---|---|---|---|---|---|---|---|---|
| Ex. 4 | hFDCA | HAc:water 70:30 | 30 | 180 | 30 | 70 | 133 | 1.9 |
| Ex. 5 | rFDCA | HAc:water 70:30 | 30 | 180 | 30 | 122 | 223 | 1.8 |
| Ex. 6 | rFDCA | HAc:water 70:30 | 30 | 180 | 60 | 127 | 257 | 2.0 |
| Ex. 7 | cFDCA | HAc:water 70:30 | 30 | 180 | 30 | 52 | 100 | 1.9 |
| Ex. 8 | cFDCA | HAc:water 70:30 | 21 | 160 | 30 | 56 | 106 | 1.9 |
| Ex. 9 | cFDCA | HAc:water 70:30 | 30 | 160 | 30 | 38 | 74 | 1.9 | was 20 wt % FDCA in water, heated to 180° C. to fully dissolve the hFDCA, and subsequent cooling to 40° C.

These samples were tested to generate a particle size distribution at 0.2 bar dispersion pressure and also at 2.0 bar dispersion pressure, in order to test the particle strength. The results are shown in Table 7 below.

TABLE 7

Comparative Examples 13 and 14

| Test | Feed | Solvent | FDCA (wt %) | T (° C.) | Cooling Rate (K/hr) | d50 µm (at 0.2 bar) | d50 µm (at 2 bar) | Relative decrease % |
|---|---|---|---|---|---|---|---|---|
| Comp. 13 | hFDCA | Water | 20 | 180 | 30 | 198 | 89.2 | 54.9 |
| Comp. 14 | hFDCA | Water | 20 | 180 | 60 | 254 | 116 | 54.3 |

B8—Examples 10 to 12—Particle Strength

Examples 10 to 12 were subjected to thermal treatment by taking a sample of FDCA which had been purified by hydrogenation (hFDCA) and subjecting it to partial dissolution and controlled crystallization, according to the conditions in the table below. In each case the sample was kept at the desired temperature for the specified time and subsequently cooled to 40° C.

These samples were tested to generate a particle size distribution at 0.2 bar dispersion pressure and also at 2.0 bar dispersion pressure, in order to test the particle strength. The results are shown in Table 8 below.

TABLE 8

Examples 10 to 12

| Test | Feed | Solvent HAc:water by weigh | FDCA (wt %) | T (° C.) | Time (hrs) | d50 µm (at 0.2 bar) | d50 µm (at 2 bar) | Relative decrease % |
|---|---|---|---|---|---|---|---|---|
| Ex. 10 | hFDCA | 70:30 | 30 | 180 | 1 | 157 | 127 | 19.1 |
| Ex. 11 | hFDCA | 95:5 | 12 | 140 | 4 | 70.5 | 55.7 | 21.0 |
| Ex. 12 | hFDCA | 95:5 | 12 | 140 | 4 | 60.6 | 49.4 | 18.5 |

Examples 10 to 12 use lower water concentrations in the treatment solvent composition and are therefore not according to the invention. However, we found the above trends also for treatment solvent compositions that comprise more than 95% by weight of water. Therefore, from the obtained data it can be assumed that for a thermal treatment according to the invention much more stable particles are obtained after thermal treatment, as indicated by the lower percentage reduction in d50 when the tests at 2.0 bar are compared to 0.2 bar dispersion pressure.

Experiment C—Thermal Treatment

Purified FDCA was prepared by hydrogenation of crude FDCA in water, followed by crystallization, cooling, filtering, and washing with water. A solvent composition was made of acetic acid and water, in a ratio of 65:35, by weight. For each experiment 30 grams of FDCA was mixed with 70 grams of solvent. The mixture was heated in an autoclave to the desired temperature and held at temperature for 60 minutes, with stirring. The mixture was then cooled rapidly, down to 40° C., prior to filtration. The filter cake was washed with the solvent, then dried and analyzed for the listed impurities. The results are shown in the table below. The estimated % of total FDCA which is dissolved at the thermal treatment temperature is also indicated. The run at 40° C. is for comparison, and not according to the invention.

TABLE 9

Comparative Example 15 and Examples 13-15

| Test | T (° C.) | % FDCA dissolved | FDCA-Me Feed (ppm) | FDCA-Me Cake (ppm) | FDCA-Me removal | FCA Feed (ppm) | FCA Cake (ppm) | FCA removal |
|---|---|---|---|---|---|---|---|---|
| Comp. 15 | 40 | 2 | 7700 | 7230 | 6% | 1330 | 1290 | 3% |
| Ex. 13 | 140 | 25 | 10300 | 4540 | 56% | 1680 | 720 | 57% |
| Ex. 14 | 160 | 37 | 10300 | 3750 | 64% | 1680 | 650 | 61% |
| Ex. 15 | 180 | 52 | 7700 | 1930 | 75% | 1330 | 410 | 69% |

Examples 13 to 15 use lower water concentrations in the treatment solvent composition and are therefore not according to the invention. However, we found that the above trends also for treatment solvent compositions that comprise more than 95% by weight of water. Therefore, from the obtained data it can be assumed that for a thermal treatment according to the invention the temperature and the degree of dissolution is relevant for the product obtained by the thermal treatment that is measured as relative removal of FDCA-Me and FCA, respectively.

Experiment D—Solvent Composition

FDCA was prepared by hydrogenation in water, followed by crystallization, cooling, filtering, and washing with water. A solvent composition was made of acetic acid and water, in varying ratio by weight, as indicated in the table. For each experiment a composition comprising 27-30 wt % FDCA was made in the desired solvent. The mixture was heated in an autoclave to 180° C. and held at temperature for 60 minutes with stirring. The mixture was then cooled rapidly, down to 40° C., prior to filtration. The filter cake was washed with the solvent, then dried and analyzed for the reported impurities. The results are shown in Table 10 below. The estimated % of total FDCA which is dissolved at the thermal treatment temperature (180° C.) is also reported.

TABLE 10

Examples 16-20

| Test | Solvent, wt/wt HAc:H2O | % dissolved | FDCA-Me Feed (ppm) | FDCA-Me Cake (ppm) | FDCA-Me removal | FCA Feed (ppm) | FCA Cake (ppm) | FCA removal |
|---|---|---|---|---|---|---|---|---|
| Ex. 16 | 95:5 | 34 | 8400 | 3000 | 64% | 820 | 220 | 73% |
| Ex. 17 | 80:20 | 36 | 7700 | 1910 | 75% | 1330 | 370 | 72% |
| Ex. 18 | 65:35 | 52 | 7700 | 1930 | 75% | 1330 | 410 | 69% |
| Ex. 19 | 55:45 | 60 | 7700 | 2180 | 72% | 1330 | 440 | 67% |
| Ex. 20 | 50:50 | 58 | 8100 | 1380 | 83% | 1030 | 260 | 75% |

Examples 16 to 20 use lower water concentrations in the treatment solvent composition and are therefore not according to the invention. However, we found the above trends also for treatment solvent compositions that comprise more than 95% by weight of water. Therefore, from the obtained data it can be assumed that for a thermal treatment according to the invention that excellent removal rates of FDCA-Me and FCA can be obtained for a broad variety of solvent compositions.

Experiment E—Crystallisation from Water after Complete Dissolution

Further comparative experiments were conducted at complete dissolution. Mixtures of FDCA were provided that were made by mixing of different purified FDCA compositions in order to generated samples with variations in FCA and FDCA-Me relative to the FDCA. The samples were prepared at a total concentration of 4 wt % of FDCA, in order to provide full dissolution at 140° C. After treatment in water the samples were cooled to crystallize the FDCA, and the cakes were analyzed for purity. The table below shows the results when recrystallizing from water.

TABLE 11

Comparative Examples 16-20

| Test | FDCA-Me Feed (ppm) | FDCA-Me Cake (ppm) | FDCA-Me removal | FCA Feed (ppm) | FCA Cake (ppm) | FCA removal |
|---|---|---|---|---|---|---|
| Comp. 16 | 690 | 670 | 3% | 10300 | 1880 | 82% |
| Comp. 17 | 1380 | 1460 | nil | 10300 | 2270 | 78% |
| Comp. 18 | 5170 | 4970 | 4% | 10400 | 3790 | 64% |
| Comp. 19 | 6860 | 6920 | nil | 10200 | 5040 | 51% |
| Comp. 20 | 13620 | 13810 | nil | 10200 | 7600 | 25% |

It can be seen from the data that the removal efficiency of FCA is improved significantly when only a limited amount of FDCA-Me is present. Also, it is seen that FDCA-Me is not removed by recrystallization from water under this conditions with essentially complete reincorporation into the cake. Comparative Experiment 20 resembles concentrations of FDCA-Me encountered in practical operation and shows a removal efficiency which in many cases will be insufficient.

The invention claimed is:

1. A process for producing a carboxylic acid composition comprising 2,5-furandicarboxylic acid, the process comprising the steps:
   a) providing or producing a crude carboxylic acid composition comprising 2,5-furandicarboxylic acid and 5-formyl-2-furancarboxylic acid;
   b) purifying the crude carboxylic acid composition to produce a purified carboxylic acid composition comprising 2,5-furandicarboxylic acid, wherein the purifying comprises at least one step selected from the group consisting of:
hydrogenating at least a portion of the 5-formyl-2-furancarboxylic acid;
oxidizing at least a portion of the 5-formyl-2-furancarboxylic acid;
recrystallization of at least a portion of the 2,5-furandicarboxylic acid; and
hydrolyzing of dialkyl ester of 2,5-furandicarboxylic acid;
c) providing or producing a treatment solvent composition comprising more than 95% by weight of water, with respect to the weight of the treatment solvent composition;
d) providing or producing a thermal treatment composition comprising the purified carboxylic acid composition and the treatment solvent composition;
e) subjecting the thermal treatment composition to an elevated temperature in the range of 140 to 200° C. for a time in the range of 5 to 240 min, wherein the percentage of dissolved 2,5-furandicarboxylic acid, relative to the total amount of 2,5-furandicarboxylic acid, is in the range of 10 to 80% to obtain a treated composition; and
f) cooling the treated composition to a temperature in the range of 20 to 80° C. and separating at least a portion of the 2,5-furandicarboxylic acid from the treated composition to obtain a carboxylic acid composition and a treatment mother liquor comprising water.

2. The process according to claim 1, wherein the crude carboxylic acid composition and/or the purified carboxylic acid composition comprise mono methyl ester of 2,5-furandicarboxylic acid.

3. The process according to claim 1,
wherein step e) is conducted in a reactor that is pressurized with an inert gas,
and/or
wherein the thermal treatment composition in step e) is agitated for at least a portion of the time to expose the solid 2,5-furandicarboxylic acid to shear forces.

4. The process s according to claim 1,
wherein the thermal treatment composition comprises 2,5-furandicarboxylic acid in an amount of 15 to 45% by weight with respect to the weight of the thermal treatment solvent composition,
and/or
wherein the treatment solvent composition comprises acetic acid and water.

5. The process according to claim 1, wherein the crude carboxylic acid composition comprises 2-furan carboxylic acid in an amount in the range of 1 to 2000 ppm by weight with respect to the weight of the composition and wherein the carboxylic acid composition comprises 2-furan carboxylic acid in an amount of not more than 700 ppm by weight.

6. The process according to claim 1, wherein the crude carboxylic acid composition comprises mono alkyl ester of 2,5-furandicarboxylic acid in an amount in the range of 0.2 to 5.0% by weight with respect to the weight of the crude carboxylic acid composition.

7. The process according to claim 1, wherein the purifying in step b) comprises the step of hydrogenating at least a portion of the 5-formyl-2-furancarboxylic acid.

8. The process according to claim 1, wherein in step e) the percentage of dissolved 2,5-furandicarboxylic acid, relative to the total amount of 2,5-furandicarboxylic acid, is in the range of 20 to 60%.

9. The process according to claim 1,
wherein the temperature in step e) is in the range of 150 to 190° C.,
and/or
wherein the thermal treatment composition in step e) is subjected to an elevated temperature for a time in the range of 15 to 120 min.

10. The process according to claim 1, wherein the treated composition in step f) is cooled to a temperature in the range of 30 to 80° C.

* * * * *